(12) United States Patent
Chen et al.

(10) Patent No.: US 10,677,805 B1
(45) Date of Patent: Jun. 9, 2020

(54) COLOR-CHANGING EYE DROPS FOR EARLY SCREENING ALZHEIMER'S DISEASE AND APPLICATION THEREOF

(71) Applicant: NATIONAL CHIAO TUNG UNIVERSITY, Hsinchu (TW)

(72) Inventors: Jung-Chih Chen, Hsinchu (TW); I-Chiu Li, Hsinchu (TW); Kun-Che Li, Hsinchu (TW); Ching-Cheng Chuang, Hsinchu (TW); Mei-Lan Ko, Hsinchu (TW); Han-Chien Chuang, Hsinchu (TW); Ming-Hung Chien, Hsinchu (TW); Yu-Rong Wang, Hsinchu (TW); Hung-Ru Wang, Hsinchu (TW)

(73) Assignee: NATIONAL CHIAO TUNG UNIVERSITY, Hsinchu (TW)

( * ) Notice: Subject to any disclaimer, the term of this patent is extended or adjusted under 35 U.S.C. 154(b) by 0 days.

(21) Appl. No.: 16/441,901

(22) Filed: Jun. 14, 2019

(51) Int. Cl.
| C07H 21/04 | (2006.01) |
| G01N 33/68 | (2006.01) |
| G01N 21/78 | (2006.01) |
| G01N 33/58 | (2006.01) |
| G01N 27/02 | (2006.01) |

(52) U.S. Cl.
CPC ......... *G01N 33/6896* (2013.01); *G01N 21/78* (2013.01); *G01N 33/587* (2013.01); *G01N 27/026* (2013.01); *G01N 2800/2821* (2013.01); *G01N 2800/50* (2013.01)

(58) Field of Classification Search
None
See application file for complete search history.

(56) References Cited

U.S. PATENT DOCUMENTS

| 9,023,607 B2 | 5/2015 | Kim et al. |
| 2013/0172700 A1 | 7/2013 | Lan et al. |
| 2014/0356859 A1* | 12/2014 | Azzazy .................. C12Q 1/04 435/5 |

OTHER PUBLICATIONS

Zhou et al. (SMALL Journal 2015, 11, No. 18, 2144-2149).*
Hagan et al. The EPMA Journal (2016) 7:15.*

* cited by examiner

*Primary Examiner* — Kimberly Chong
(74) *Attorney, Agent, or Firm* — Rosenberg, Klein & Lee

(57) ABSTRACT

The invention relates to color-changing eye drops for early screening Alzheimer's disease and an application thereof. The color-changing eye drop for early screening Alzheimer's disease comprises 1 pg/ml to 10 ng/ml of $A\beta_{42}$ aptamer-gold nanoparticles (AuNPs) and a pharmaceutically acceptable carrier or vehicle thereof, which can be used to mix with a tear sample of a test subject to analyze a color change of the color-changing eye drop for determining the concentration proportion of $A\beta_{40}$:$A\beta_{42}$ contained in the tear sample of the test subject.

2 Claims, 2 Drawing Sheets
(2 of 2 Drawing Sheet(s) Filed in Color)
Specification includes a Sequence Listing.

SEQUENCE LISTING

<160> NUMBER OF SEQ ID NOS: 1

<210> SEQ ID NO 1
<211> LENGTH: 42
<212> TYPE: PRT
<213> ORGANISM: Homo sapiens
<220> FEATURE:
<223> OTHER INFORMATION: Ab42 aptamer

<400> SEQUENCE: 1

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40
```

US 10,677,805 B1

COLOR-CHANGING EYE DROPS FOR EARLY SCREENING ALZHEIMER'S DISEASE AND APPLICATION THEREOF

BACKGROUND OF THE INVENTION

1. Field of the Invention

The present invention relates to provide color-changing eye drops for early screening Alzheimer's disease and an application thereof which can be used to quickly and early screen whether a test subject has the symptom of Alzheimer's disease, and has the advantages of low cost and convenience in use.

2. Description of Related Art

Dementia is a brain disease that results from the degeneration and shrinkage of brain cells, leading to brain dysfunctions and gradual decrease in memory and even affecting daily activities when patients are in the late stages.

Alzheimer's disease (AD) is the most common form of dementia, which accounts for 50-60% of dementia cases, followed by vascular dementia (about 20%) caused by cerebral vascular occlusion, mixed dementia (about 10%) due to the coexistence of Alzheimer's disease and brain stroke, and dementia caused by other conditions (about 10%), e.g. Parkinson's disease, hydrocephalus, head trauma, syphilis, AIDS, depression, or environmental toxins. Early symptoms of Alzheimer's disease include memory loss due to deposition of amyloid plaques in the brain. According to the report of the Alzheimer's Association, the ratio of $A\beta_{40}:A\beta_{42}$ in normal human cerebrospinal fluid is 9:1, whereas the ratio of $A\beta_{40}:A\beta_{42}$ in AD patients is 1:1.

Due to the large population of dementia in the world, scholars from various countries are committed to relevant research for purposes of treating or detecting dementia. According to the report (*The Global Impact of Dementia, World Alzheimer Report* 2018), dementia community is likely to rise to about 152 million people by 2050, to one that's more the size of Russia or Bangladesh. The current cost of the disease is about a trillion US dollars a year, and that's forecast to double by 2030. At present, there is no effective treatment for Alzheimer's disease which accounts for 50-60% of dementia. Therefore, various tools for screening Alzheimer's disease still need to be developed to screen the patients before the onset of serious signs so as to delay the progression of brain cell degeneration by early treatment.

For instance, the U.S. Pat. No. U.S. Pat. No. 9,023,607B2, issued on 5 May 2015, has disclosed a method for early diagnosis of Alzheimer's disease using phototransistor. It mainly uses a phototransistor device for detecting the presence of beta-amyloid in cells. The method comprises the steps of providing cells that potentially contain beta-amyloid; labeling the cells with a protein biomarker characteristic of Alzheimer's disease (preferably beta-amyloid) by magnetic beads; locating the cells in a channel region of the phototransistor; and detecting a difference in photocurrent between normal cells and the cells comprising the protein biomarker labeled with magnetic beads to diagnose Alzheimer's disease in an early stage. However, the above method is complicated in the preparation process of the magnetic beads. In addition, due to the use of the phototransistor device, the assistance of a professional skilled in the phototransistor device is indispensable to detect or analyze the results.

Besides, the U.S. Pat. Pub. No. US20130172700A1, published on 4 Jul. 2013, has disclosed an optical detection method which detects the concentration of beta-amyloid in the human eye by a non-invasive and non-labeled in vitro test. Specifically, the method comprises the steps of: selecting β-amyloid (Aβ) as the substance; emitting a light with a wavelength of 300-330 nm to a testing area in the eye, wherein a frequency of the light is selected according to an absorption spectrum of the selected substance, and the frequency is equal or close to a resonant excitation frequency of one of the electronic molecular energy levels of the substance, so as to excite the substance to generate resonance-enhanced Raman effect or pre-resonance Raman effect to form a detection spectrum; and receiving the detection spectrum and estimating the concentration of the substance according to a peak intensity of the detection spectrum. Although the above method detects the concentration of β-amyloid in the human eye in a non-invasive manner, the above method still involves expensive optical instruments and requires a professional to operate optical instruments and interpret the spectral meaning of the detection. Therefore, the above method still lacks convenience in use.

SUMMARY OF THE INVENTION

In view of the above-mentioned problems, the object of the present invention is to provide color-changing eye drops for early screening Alzheimer's disease and an application thereof which can be used for quickly and early screening whether a test subject has the symptom of Alzheimer's disease by mixing with a tear sample of the test subject to analyze a color change of the color-changing eye drop.

Disclosed herein is a color-changing eye drop for early screening Alzheimer's disease, comprising 1 pg/ml to 10 ng/ml of $A\beta_{42}$ aptamer-gold nanoparticles (AuNPs) and a pharmaceutically acceptable carrier or vehicle thereof. Preferably, the $A\beta_{42}$ aptamer comprises the amino acid sequence of SEQ ID NO:1.

Furthermore, a method for early screening Alzheimer's disease by use of the color-changing eye drop as described above is also disclosed herein. It comprises the steps of: mixing the color-changing eye drop with a tear sample of a test subject; and analyzing a color change of the color-changing eye drop for determining a concentration proportion of $A\beta_{40}:A\beta_{42}$ contained in the tear sample of the test subject.

Accordingly, the present invention can be used to rapid and early detect whether the test subject has a sign of Alzheimer's disease without the need to use expensive instruments for detection.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENT

Figure 1:
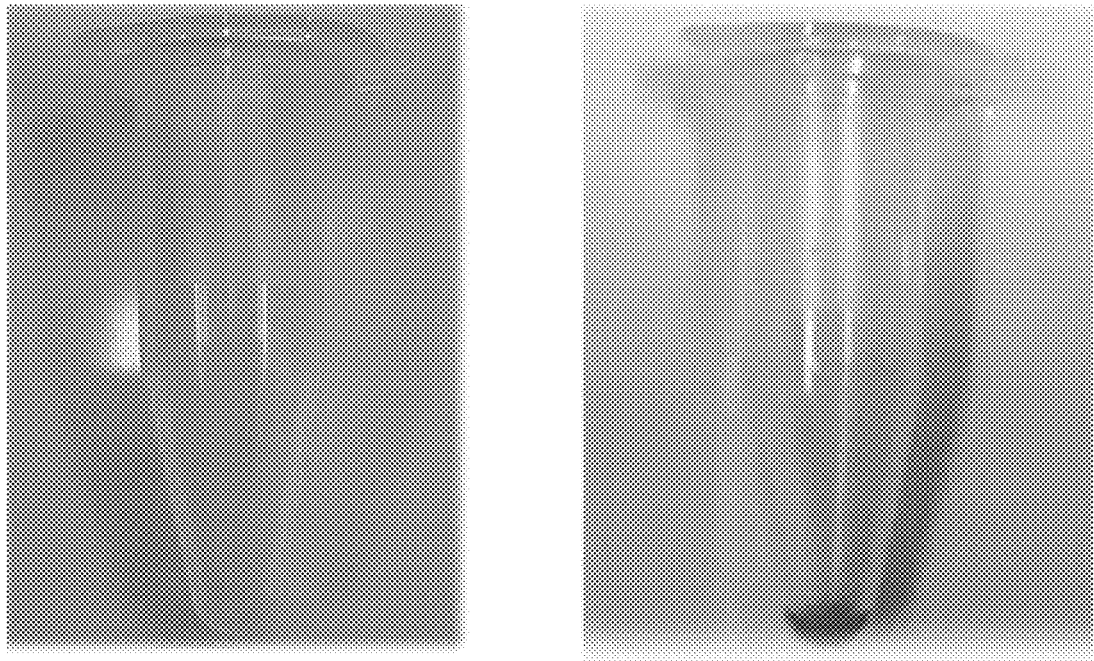
FIG. 1 is a schematic diagram showing a color change of color-changing eye drops mixed with a tear sample containing $A\beta_{42}$.

The present invention relates to color-changing eye drops for early screening Alzheimer's disease and an application thereof. The color-changing eye drop for early screening Alzheimer's disease disclosed herein comprises 1 pg/ml to 10 ng/ml of $A\beta_{42}$ aptamer-gold nanoparticles (AuNPs) and a pharmaceutically acceptable carrier or vehicle thereof. Preferably, the $A\beta_{42}$ aptamer comprises the amino acid sequence of SEQ ID NO:1.

Additionally, the method for early screening Alzheimer's disease by use of the color-changing eye drop as described above comprises the steps of: mixing the color-changing eye drop with a tear sample of a test subject; and analyzing a color change of the color-changing eye drop for determining a concentration proportion of $A\beta_{40}$:$A\beta_{42}$ contained in the tear sample of the test subject.

Hereinafter, an exemplary embodiment of the present invention will be described in detail with reference to the accompanying drawings.

The present invention used the existing electrochemical impedance spectroscopy (EIS) to analyze the ratio of $A\beta_{40}$:$A\beta_{42}$ concentration. Prior to the establishment of a calibration curve of the $A\beta_{40}$ and a calibration curve of the $A\beta_{42}$, the specificity of the $A\beta_{40}$ antibody and the specificity of the $A\beta_{42}$ antibody were first confirmed. Then, various solutions of 100 pg, 1 ng, 10 ng, 100 ng, 1 μg, and 10 μg were prepared by using commercially available $A\beta_{40}$ protein and $A\beta_{42}$ protein dissolved in PBS solvent. A tear sample was separately dropped into a wafer containing $A\beta_{40}$ antibodies and a wafer containing $A\beta_{42}$ antibodies to obtain the impedance difference between the $A\beta_{40}$ protein and the $A\beta_{4}2$ protein, and the impedance difference was substituted into the calibration curves of $A\beta_{40}$ and $A\beta_{42}$, respectively, thereby obtaining the concentration proportion of $A\beta_{40}$ and $A\beta_{42}$ in the tear sample. After the parameter of the $A\beta_{40}$:$A\beta_{42}$ ratio were confirmed, the parameter was used as a base to prepare aptamer with specific range of color change.

Example 1: Preparing $A\beta_{42}$ Aptamer-Gold Nanoparticles (AuNPs)

1. Preparation of $A\beta_{42}$ Aptamer

In general, $A\beta_{42}$ antibodies only specifically bind $A\beta_{42}$ in the sample without binding to $A\beta_{40}$. However, the traditional antibodies are quite expensive and difficult to store, and the procedure for manufacturing antibodies into detection reagents or test kits is complicated. Therefore, the present invention established an $A\beta_{42}$ aptamer to replace the traditional antibody, so as to achieve specific binding to $A\beta_{42}$ as well as $A\beta_{40}$ and improve the convenience of preservation.

In this example, systematic evolution of ligands by exponential enrichment (SELEX) was used to prepare an $A\beta_{42}$ aptamer as set forth in SEQ ID NO: 1.

2. Bonding $A\beta_{42}$ Aptamers with Gold Nanoparticles (AuNPs)

Gold (Au) nanoparticles has excellent biocompatibility and surface plasmon resonance. Therefore, gold nanoparticles (AuNPs) are commonly used in biomedical detection, disease diagnosis and gene detection.

In this example, $A\beta_{42}$ aptamer-gold nanoparticles (AuNPs) were prepared by reference to journals published by Wen Yun et al. (European Food Research and Technology 238(6):989-995) and published by Lin, Xiaoyan et al. (Chem Sci. 2017 May 1; 8(5):3905-3912).

Primarily, sodium citrate was added as a reducing agent to chloroauric acid ($HAuCl_4$) to prepare gold nanoparticles. A 100 mL solution containing 0.01 g of chloroauric acid was refluxed, and 2.5 mL of a 1% sodium citrate solution was added to the chloroauric acid solution while stirring the chloroauric acid solution to form a mixed solution. Then, the mixed solution was boiled for 30 minutes, cooled to room temperature, and stored in a dark glass bottle at 4° C. for use. $A\beta_{42}$ aptamers was added to 10 mM TCEP (tris(2-carboxyethyl)phosphine) solution for 30 minutes at room temperature for reaction, and then 100 nM reaction $A\beta_{42}$ aptamers, 0.01% tween 20 and 200 nM PEG-thiol were added to 50 nM gold nanoparticles and reacted at room temperature for 1.5 hours. After the reaction, the mixture was centrifuged at 12,000 rpm for 30 minutes, and the supernatant includes a complex of $A\beta_{42}$ aptamer-gold nanoparticles (Aptamer-AuNPs).

Example 2: Using Aptamer-AuNPs for Detection

In this example, the color-changing eye drops were used to detect the color change of a tear sample of a normal test subject. The tear sample were collected by using a strip paper that prevents tears from sucking back, and the tear collection strip was placed in a centrifuge tube and centrifuged at a speed of 13,000 rpm to obtain about 10 μl of the tear sample. Then, 10 μl of tear sample was mixed with 10 μl of Aptamer-AuNPs solution for reaction for 10 minutes. According to the report of the Alzheimer's Association, the ratio of $A\beta_{40}$:$A\beta_{42}$ in normal human cerebrospinal fluid is 9:1, whereas the ratio of $A\beta_{40}$:$A\beta_{42}$ in AD patients is 1:1. When the ratio of $A\beta_{40}$ to $A\beta_{42}$ in the tear sample is not 9:1, the color of the Aptamer-AuNPs will be changed, which can be used to preliminarily determine the symptom of Alzheimer's disease. Furthermore, the degree of change in the color of Aptamer-AuNPs with the ratio of $A\beta_{40}$:$A\beta_{42}$ from 9:1 to 1:1 can be further measured by spectrophotometry.

Referring to FIG. 1, the color-changing eye drops of the present invention exhibit a color change (blue) after the addition of $A\beta_{42}$-containing tear sample. Accordingly, the color-changing eye drops can be added to the tear sample isolated from the test subject, or directly dropped into the eyes of the test subject, to rapidly screen whether the test subject has the symptom of Alzheimer's disease based on color change, e.g. excessively high $A\beta_{42}$ concentration.

Figure 2:
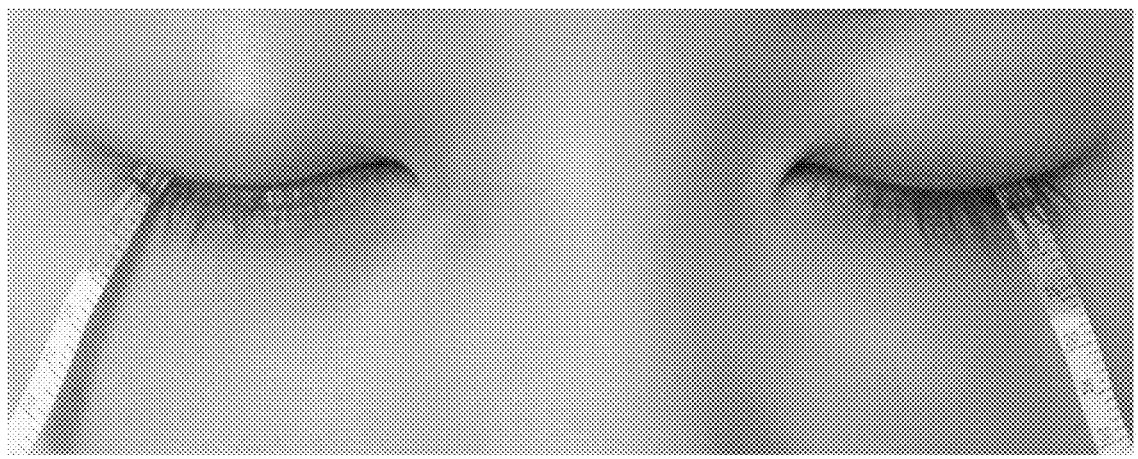
FIG. 2 is a schematic diagram showing an application of color-changing eye drops to a test strip for detection.

Referring to FIG. 2, the color-changing eye drops of the present invention can also be dropped onto a test strip, and then the tear sample of the test subject is absorbed by the test strip to detect whether a color change occurs. As shown in FIG. 2, the color change of the test strip indicates that the normal test subject contains $A\beta_{42}$ in the tear sample. If the test subject has a high concentration of $A\beta_{42}$ that changes the general ratio of $A\beta_{40}$:$A\beta_{42}$ of 9:1, the color change of the test strip will be more obvious and can be determined that there is a symptom of Alzheimer's disease.

Compared with the technique available now, the present invention has the following advantages:

1. The present invention uses the $A\beta_{42}$ aptamer-gold nanoparticles to specifically recognize $A\beta_{42}$, which solves the problem that the traditional antibodies are quite expensive, not easy to store, and difficult to be made into detection reagents or detection kits.

2. The present invention quickly and easily detects whether a sample has a high concentration of $A\beta_{42}$ by color change and does not require expensive instruments for detecting or analyzing the results.

3. The invention is made into an eye drop type, so that people can observe the color change after the eye drops are dripped into the eye in daily life for preliminary monitoring whether the signs of Alzheimer's disease appear. Therefore, the present invention can be conveniently used to initially monitor the occurrence of the symptom of Alzheimer's disease, and only when the test results show that people have the symptom of Alzheimer's disease, they need to go to the hospital for further examination.

What is claimed is:

1. A method for early screening Alzheimer's disease by use of a color changing eye drop, comprising:
   (a) preparing $A\beta_{42}$ aptamer containing amino acid sequence of SEQ ID NO:1,
   (b) bonding the prepared $A\beta_{42}$ aptamer with gold nanoparticles (AuNPs) to obtain a complex of $A\beta_{42}$ aptamer-gold nanoparticles (Aptamer-AuNPs),
   (c) formulating a color-changing eye drop containing Aptamer-AuNPs in a range of 1 pg/ml-10 ng/ml and a pharmaceutically acceptable carrier thereof,
   (d) mixing approximately 10 μl of the color-cha aging eye drop with approximately 10 μl of a tear sample of a test by a technique selected from a group containing mixing in a centrifuge tube, using a test strip, dropping the color-changing eye drop into at least one eye of the test subject, and combination thereof, for a reaction time of approximately 10 minutes,
   (e) analyzing a color of the color-changing eye drop mixed with the tear sample; and
   (f) if the color of the mixture of the color-changing eye drop and the tear sample has changed, a concentration proportion of $A\beta_{40}$:$A\beta_{42}$ contained in the tears ample of the test subject in a range 9:1-1:1.

2. The method for early screening Alzheimer's disease by use of a color-changing eye drop as claimed in claim 1, further comprising:
   in said step (e), anal zing the color of the color-changing drop mixed with the tear sample by spectrophotometry, and
   in said step (f), indicating a possible presence of the Alzheimer's disease if said concentration proportion of the $A\beta_{40}$:$A\beta_{42}$ has excessively high $A\beta_{42}$ concentration corresponding to a deviation of said proportion $A\beta_{40}$:$A\beta_{42}$ from 9:1 in the range from 9:1 to 1:1.

* * * * *